United States Patent [19]

Yokoyama et al.

[11] 4,425,319

[45] Jan. 10, 1984

[54] RADIOACTIVE DIAGNOSTIC AGENT AND NON-RADIOACTIVE CARRIER THEREFOR

[75] Inventors: Akira Yokoyama, Otsu; Yoshiro Omomo, Kyoto; Hisashi Tanaka, Ashiya; Hideo Saji, Kyoto, all of Japan

[73] Assignee: Nihon Medi-Physics Co., Ltd., Hyogo, Japan

[21] Appl. No.: 236,520

[22] Filed: Feb. 20, 1981

[30] Foreign Application Priority Data

Mar. 8, 1980 [JP] Japan ................................. 55-29471

[51] Int. Cl.³ ...................... A61K 43/00; A61K 49/00
[52] U.S. Cl. .................................. 424/1.1; 260/112 B; 260/429 R; 128/659; 424/9
[58] Field of Search ..................... 424/1, 9; 128/659; 260/112 B, 429 R

[56] References Cited

U.S. PATENT DOCUMENTS 3,961,038 6/1976 Benes ...................................... 424/1

OTHER PUBLICATIONS

Sephton et al., Proc. Soc. Exp. Biol. Med., 161, 402–406 (1979).
Hemmaplardh et al., Biochim. Biophys. Acta, 373, 84–99 (1974).
Yokomana et al., Int. J. Appl. Rad. Isotopes, 26, 291–299 (1975).
Oster et al., J. Nucl. Med., 21, 421–425 (1980).
Goodman et al., J. Label. Comp. Radiophar., 16, 138–139 (1979).
Steinling et al., Lille Med., 24, 82–85 (1979).
Larson et al., Radiology, 130, 241–244 (1979).
Chandra et al., Radiology, 128, 697–699 (1978).
Hoffer et al., Radiology, 131, 775–779 (1979).
Hoffer et al., J. Nucl. Med., 20, 248–251 (1979).
Oster, J. Nucl. Med., 19, 732, (1978).

*Primary Examiner*—Christine M. Nucker
*Attorney, Agent, or Firm*—Birch, Stewart, Kolasch & Birch

[57] ABSTRACT

A radioactive diagnostic agent which comprises deferoxamine, and a physiologically active compound and a radioactive metallic element chemically connected thereto with or without intervention of any other chemical bonding, which is characteristic in having a high stability even after being administered into a human body and showing substantially the same behavior in a human body as said physiologically active compound itself.

22 Claims, No Drawings

RADIOACTIVE DIAGNOSTIC AGENT AND NON-RADIOACTIVE CARRIER THEREFOR

The present invention relates to a radioactive diagnostic agent and a non-radioactive carrier therefor. More particularly, it relates to a radioactive diagnostic agent comprising deferoxamine, and a physiologically active substance and a radioactive metallic element bonded thereto, and a non-radioactive carrier comprising deferoxamine, and a physiologically active substance bonded thereto which is useful for preparation of said radioactive diagnostic agent.

For the purpose of non-invading nuclear medical diagnosis such as recording, dynamic study and quantitative measurement of a blood circulation system, detection of physiological abnormality or localization of abnormality by imaging, there have been used various physiologically active substances labeled with iodine-131 ($^{131}$I). For instance, $^{131}$I-labeled human serum albumin has been used for recording and dynamic study of a blood circulation system. Further, for instance, $^{131}$I-labeled fibrinogen has been used for detection of thrombus. However, $^{131}$I has a long half life of about 8 days and emits beta-rays in addition to gamma-rays useful for diagnosis so that a patient administered therewith is exposed to a large quantity of radiation.

Because of the above drawback inherent to $^{131}$I, various attempts have been made to provide radioactive diagnostic agents not having such drawback by introducing other radioactive metallic elements more suitable for nuclear medical diagnosis into physiologically active substances in appropriate procedures. Among them, the most notable is a direct labeling method wherein any salt of a radioactive metallic element is treated with a physiologically active substance to form a chelate compound between them. For instance, technetium-99m ($^{99m}$Tc) in the form of pertechnetate is treated with human serum albumin in the presence of a reducing agent in an aqueous medium to give $^{99m}$Tc-labeled human serum albumin. Further, for instance, indium-111 ($^{111}$In) in the form of indium chloride is treated with bleomycin in an aqueous medium to give $^{111}$In-labeled bleomycin. However, the chelate-forming ability of these physiologically active substances to be labeled is not always sufficient, and the labeled products are frequently decomposed in living bodies. Thus, the behavior of the radioactive metallic element in living bodies does not coincide with that of the physiologically active substance. This is a critical defect for the purpose of nuclear medical diagnosis.

As understood from the above defect, there has been highly demanded the appearance of a technique which can label a physiologically active substance with a radioactive metallic element by a simple operation to afford a radioactive metal-labeled product which retains substantially the physiological activity attributed to the physiologically active substance and yet keeps stable the bonding between the physiologically active substance and the radioactive metallic element so that the radioactive metal-labeled product behaves in a living body in substantially the same manner as the physiologically active substance itself, and the exact trace as well as the precise diagnosis are made possible.

As the result of an extensive study, it has now been found that the use of deferoxamine as a bonding agent between a physiologically active substance and a radioactive metallic element can provide a radioactive diagnostic agent which meets the said demand. Namely, deferoxamine can be bonded chemically with a physiologically active substance with or without intervention of any other chemical bonding and also bound with a radioactive metallic element through a chelating bond to give a radioactive metal-labeled physiologically active product which is characteristic in having a stable bonding between the radioactive metallic element and the physiologically active substance due to the presence of the deferoxamine molecule and showing substantially the same behavior in a living body as the physiologically active substance itself.

According to the present invention, there is provided a non-radioactive carrier for a radioactive metal comprising deferoxamine and a physiologically active substance chemically bonded thereto with or without intervention of any other chemical bonding. There is also provided a radioactive diagnostic agent comprising deferoxamine, a physiologically active substance chemically bonded thereto with or without intervention of any other chemical bonding and a radioactive metallic element bonded to deferoxamine through a chelating bond.

For preparation of the non-radioactive carrier of the invention, deferoxamine may be treated with a physiologically active substance to combine them by a chemical bond.

Deferoxamine, i.e. 1-amino-6,17-dihydroxy-7,10,18,21-tetraoxo-27-(N-acetylhydroxylamino)-6,11,17,22-tetraazaheptaeicosane, is a known compound (cf. The Merck index, 9th Ed., page 374 (1976)). It may be used in a free form or a salt form (e.g. hydrochloride, methanesulfonate). It may be also used in any crystalline form including crystalline water.

Any active group (e.g. amino, carbonyl, hydroxyl) in deferoxamine may be utilized for formation of the chemical bond. In general, however, many physiologically active substances are sensitive to heat, and the application of a relatively high reaction temperature and/or a relatively long reaction time should be avoided. From this viewpoint, the amino group in deferoxamine is the most frequently utilized, because it has a comparatively high reactivity and the reaction therewith can proceed under a relatively mild condition.

As the physiologically active substance, there may be used any one which can be accumulated in a certain specific tissue or organ or can take any certain specific behavior depending upon the physiological status or condition of a living body. Examples of the physiologically active substance are organic substances such as proteins (e.g. human serum albumin, urokinase, fibrinogen), antibiotics (e.g. bleomycin, kanamycin), hormones, saccharides, fatty acids, etc. Among them, those having any reactive group (e.g. carboxyl) with an amino group is the most advantageous. Even if the physiologically active substance itself does not have such reactive group, the one into which such reactive group can be readily set up is also used advantageously. Further, the use of any bonding aid is often effective to establish a favorable chemical bonding between deferoxamine and the physiologically active substance.

When, for instance, the physiologically active substance has an active carboxyl group, an amino group in deferoxamine is reacted with the carboxyl group to form a carbonamide linkage (—CONH—), whereby deferoxamine and the physiologically active substance are bonded together. This reaction may be achieved by a per se conventional procedure for formation of a carbonamide linkage between an amino group and a carboxyl group. For instance, the reaction can smoothly proceed in the presence of a condensing agent such as a water-soluble carbodiimide (e.g. 1-cyclohexyl-3-(2-morpholinyl-4-ethyl)carbodiimide, 1-ethyl-3-(3-dimethylaminopropyl)carbodiimide).

When, for instance, the physiologically active substance has an active amino group, such physiologically active substance and deferoxamine may be subjected to reaction with any compound having at least two carbonyl groups such as glutaraldehyde, whereby they are bound together by formation of an aldimine linkage (—CH=N—) or a ketimine linkage (>C=N—) between the physiologically active substance and the glutaraldehyde and also between the glutaraldehyde and the deferoxamine. Then, the resultant intermediary product is subjected to reduction by a per se conventional procedure appliable to a Schiff's base, for instance, using a metal hydride (e.g. sodium borohydride).

The reaction product from the above bonding reaction may be, if necessary, purified by a per se conventional procedure such as dialysis or gel filtration so as to eliminate impurities such as unreacted reagents therefrom.

The produced non-radioactive carrier is usually obtained in the form of aqueous solution, and this aqueous solution may be as such used for labeling with a radioactive metallic element. Alternatively, the aqueous solution may be subjected to lyophilization, evaporation under reduced pressure at low temperatures or the like to obtain a dried product, which can be also used as such for labeling. Depending on the use, the said aqueous solution or the said dried product may be incorporated with any additive such as an oxidation inhibitor (e.g. ascorbic acid), an isotonizing agent (e.g. sodium chloride) or a preserving agent (e.g. benzyl alcohol).

The above obtained non-radioactive carrier is per se quite stable and can be readily labeled with a radioactive metallic element by a simple operation as hereinafter explained, and therefore it may be stored and supplied with any source for a radioactive metallic element for labeling on the demand.

For labeling of the non-radioactive carrier with a radioactive metallic element (e.g. gallium-67 ($^{67}Ga$), $^{99m}Tc$, $^{111}In$, thallium-201 ($^{201}Tl$)), such carrier may be treated with the radioactive metallic element in an appropriate form, usually in an aqueous medium. When, for instance, the radioactive metallic element is $^{67}Ga$, the carrier may be treated with $^{67}Ga$ in the form of gallium chloride in an aqueous medium. When required, an oxidizing agent or a reducing agent may be present in the aqueous medium for producing an atomic valency of the radioactive metallic element which is necessitated for formation of a chelating bond. Besides, on convenience for preparation, an oxidation inhibitor (e.g. ascorbic acid), an isotonizing agent (e.g. sodium chloride) or the like may be incorporated into the aqueous medium. The presence of these substances will not materially afford any unfavorable influence on the labeling. No particular limitation is present on the radioactivity of $^{67}Ga$ to be used but it is preferred to be sufficient for obtaining the required information from the patient administered therewith through the nuclear medical diagnosis while suppressing the exposure of the patient to radiation as low as possible. The thus produced radioactive diagnostic agent is sufficiently stable, and therefore it may be stored as such and supplied on the demand.

The radioactive diagnostic agent of this invention is used for nuclear medical diagnosis. For instance, $^{67}Ga$-labeled, human serum albumin-combined deferoxamine can be used for recording, dynamic study and quantitative measurement of a blood circulation system by administering intravenously to a human body. Further, for instance, $^{67}Ga$-labeled, fibrinogen-combined deferoxamine or $^{67}Ga$-labeled, urokinase-combined deferoxamine may be used for detection and recording of thrombosis as well as localization of thrombosis, since they accumulate at the locus of thrombosis. Furthermore, for instance, $^{111}In$-labeled, streptokinase-combined deferoxamine is useful for determination of the locus of myocardial infarction. Moreover, for instance, $^{111}In$-labeled, thyroid stimulating hormone-combined deferoxamine is useful for detection and recording of a cancer at the thyroid gland.

Practical and presently preferred embodiments of the invention are illustratively shown in the following Examples wherein % is by weight, unless otherwise defined.

EXAMPLE 1

Preparation of human serum albumin-combined deferoxamine

Deferoxamine was dissolved in a mixture of 0.01 M phosphate buffer and 0.15 M aqueous sodium chloride solution (pH 7.4) (hereinafter referred to as "PBS") to make a concentration of $1.2 \times 10^{-4}$ mol/ml. To the resultant solution, glutaraldehyde (25% aqueous solution) was added to make an equimolar concentration to deferoxamine and, after 10 minutes, stirred at room temperature to give a solution (A). Separately, human serum albumin (lyophilized; 266 mg) was dissolved in PBS (20 ml) to give a solution (B). The solution (B) was admixed with the solution (A) (0.3 ml) at a temperature of 0° to 4° C., and stirring was continued at the same temperature as above for about 1 hour. To the resultant mixture, sodium borohydride (5 mg) was added, and stirring was further continued at a temperature of 0° to 4° C. for about 1 hour, whereby reduction proceeded. The reaction mixture was subjected to column chromatography on Sephadex G-50 (5×20 cm) using PBS as an eluting solution for elimination of unreacted materials, etc. to give a human serum albumin-combined deferoxamine solution as a pale yellow clear solution.

All the above operations were effected under sterile conditions.

EXAMPLE 2

Preparation of human serum albumin-combined deferoxamine

Deferoxamine was dissolved in water (1 ml) to make a concentration of $1.2 \times 10^{-4}$ mol/ml. To the resultant solution, an aqueous solution of 1-ethyl-3-(3-dimethylaminopropyl)carbodiimide ($1.2 \times 10^{-3}$ mol/ml) (1.0 ml) was added, pH was adjusted to 4.7 and stirring was continued at a temperature of 0° to 4° C. for about 30 minutes to give a solution (A). Separately, human serum albumin (lyophilized; 822 mg) was dissolved in 0.01 M phosphate buffer (pH 5.0; 30 ml) to give a solution (B). The solutions (A) and (B) were mixed together and stirred at a temperature of 0° to 4° C. for about 2 hours. The reaction mixture was admitted in a conventional dialyzing tube and subjected to dialysis for 30 hours, followed by lyophilization to give human serum albumin-combined deferoxamine as pale yellow cotton-like crystals. When dissolved in water, it gave a pale yellow clear solution.

EXAMPLE 3

Preparation of urokinase-combined deferoxamine

As in Example 1 but using purified urokinase (lyophilized; molecular weight, about 55,000; 200 mg) in place of human serum albumin, the procedure was carried out to give an urokinase-combined deferoxamine solution as a pale yellow clear solution.

EXAMPLE 4

Preparation of fibrinogen-combined deferoxamine

Fibrinogen (lyophilized; 100 mg) was dissolved in PBS (20 ml) to give a solution (A). Separately, deferoxamine mesylate (5.8 mg) was dissolved in PBS (1 ml), 1% glutaraldehyde (0.09 ml) was added thereto to make an equimolar concentration to deferoxamine, and the resultant mixture was stirred at room temperature for 10 minutes to give a solution (B). The solutions (A) and (B) were combined together, and stirring was continued at a temperature of 0° to 4° C. for 30 minutes. After addition of sodium borohydride (2 mg), stirring was continued at the same temperature as above for 30 minutes. The reaction mixture was subjected to column chromatography on Sephadex G-50 (2.2×30 cm) using PBS as an eluting solution for elimination of unreacted materials, etc. to give a fibrinogen-combined deferoxamine solution.

EXAMPLE 5

Preparation of $^{67}$Ga-labeled, human serum albumin-combined deferoxamine

To the human serum albumin-combined deferoxamine solution as prepared in Example 1 (5.7 mg of human serum albumin/ml; 2 ml), a 0.01 N hydrochloric acid solution (1 ml) containing $^{67}$Ga (1 mCi) in the form of gallium chloride was added to give a $^{67}$Ga-labeled, human serum albumin-combined deferoxamine solution as a pale yellow clear solution (pH 7.0).

EXAMPLE 6

Preparation of $^{111}$In-labeled, human serum albumin-combined deferoxamine

To the human serum albumin-combined deferoxamine solution as prepared in Example 1 (5.7 mg of human serum albumin/ml; 2 ml), a 0.01 N hydrochloric acid-physiologically saline solution (1 ml) containing $^{111}$In (1 mCi) in the form of indium chloride was added to give a $^{111}$In-labeled, human serum albumin-combined deferoxamine solution as a pale yellow clear solution (pH 7.0).

EXAMPLE 7

Preparation of $^{111}$In-labeled, urokinase-combined deferoxamine

To the urokinase-combined deferoxamine solution as prepared in Example 3 (5.0 mg of purified urokinase/ml; 2 ml), a 0.01 N hydrochloric acid solution (1 ml) containing $^{111}$In (1 mCi) in the form of indium chloride was added to give a $^{111}$In-labeled, urokinase-combined deferoxamine solution as a pale yellow clear solution (pH 7.0).

EXAMPLE 8

Preparation of $^{67}$Ga-labeled, fibrinogen-combined deferoxamine

To the fibrinogen-combined deferoxamine solution as prepared in Example 4 (1 mg of fibrinogen/ml; 1 ml), a 0.01 N hydrochloric acid solution (0.1 ml) containing $^{67}$Ga (1 mCi) in the form of gallium chloride was added to give a $^{67}$Ga-labeled, fibrinogen-combined deferoxamine solution (pH 7.2).

EXAMPLE 9

Properties of $^{67}$Ga-labeled, human serum albumin-combined deferoxamine

In order to examine the labelling efficiency of $^{67}$Ga-labeled, human serum albumin-combined deferoxamine prepared in Example 5, its aqueous solution was subjected to thin layer chromatography using cellulose as a retention material and 85% methanol as a developing solvent, and scanning was carried out by the use of a radiochromato-scanner. The radioactivity was recorded as a single peak at the original point. Any peak due to a radioactive impurity such as free gallium ion or $^{67}$Ga-deferoxamine chelate was not recognized.

From the above results, it may be said that $^{67}$Ga-labeled, human serum albumin-combined deferoxamine prepared in Example 5 has a labeling efficiency of nearly 100%.

EXAMPLE 10

Behaviors of $^{67}$Ga-labeled, human serum albumin-combined deferoxamine in rats The $^{67}$Ga-labeled, human serum albumin-combined deferoxamine solution prepared in Example 5 (0.2 ml) was administered intravenously to each of female rats of SD strain, and the variation of the blood level with the lapse of time was recorded. For the control, the same examination as above was carried out by the use of conventional $^{131}$I-labeled, human serum albumin and conventional $^{99m}$Tc-labeled, human serum albumin.

The results are shown in Table 1 wherein the blood level at each measuring time is indicated by a relative value (in average) to that immediately after the administration which is taken as 1.0.

TABLE 1

| | Variation of blood level in rats | | | |
| --- | --- | --- | --- | --- |
| | Time after administration (hours) | | | |
| No.*1 | 0 | 0.5 | 1 | 2 |
| 1 | 1.0 | 0.94 | 0.88 | 0.74 |
| 2 | 1.0 | 0.86 | 0.82 | 0.52 |
| 3 | 1.0 | 0.44 | 0.32 | — |

Note:
*1No. 1, product in Example 5;
No. 2, conventional $^{131}$I-labeled, human serum albumin;
No. 3, conventional $^{99m}$Tc-labeled, human serum albumin.

From the above results, it is understood that $^{67}$Ga-labeled, human serum albumin-combined deferoxamine according to the invention shows a much higher blood level for a longer period of time than conventional $^{131}$I-labeled, human serum albumin and conventional $^{99m}$Tc-labeled, human serum albumin. Thus, the $^{67}$Ga-labeled radioactive diagnostic agent of the invention is highly stable in a living body and is quite suitable for nuclear medical diagnosis such as recording, dynamic study and quantitative measurement of a blood circulating system.

EXAMPLE 11

Properties of $^{111}$In-labeled, urokinase-combined deferoxamine

The enzymatic activity of $^{111}$In-labeled, urokinase-combined deferoxamine prepared in Example 7 was measured by the ester decomposition method using N-α-acetyl-L-lysine methyl ester, and it was determined to have an enzymatic activity of 95% based on purified urokinase as the starting material.

From the above results, it is understood that $^{111}$In-labeled, urokinase-combined deferoxamine according to the invention retains almost the enzymatic activity of purified urokinase used as the starting material, and the behavior of the $^{111}$In-labeled radioactive diagnostic agent of the invention in a living body would be nearly the same as that of urokinase.

EXAMPLE 12

Stability of human serum albumin-combined deferoxamine

The human serum albumin-combined deferoxamine solution prepared in Example 1 was stored in a refrigerator (4° to 8° C.) for 40 days and then used for preparation of a $^{67}$Ga-labeled, human serum albumin-combined deferoxamine solution according to the procedure in Example 5. The thus obtained radioactive diagnostic agent was subjected to thin layer chromatography as in Example 9 and also subjected to examination of the behavior in rats as in Example 10. In both cases, the results were substantially the same as those obtained with a radioactive diagnostic agent prepared in the same manner as above but without storage in a refrigerator.

EXAMPLE 13

Stability of $^{67}$Ga-labeled, human serum albumin-combined deferoxamine

The $^{67}$Ga-labeled, human serum albumin-combined deferoxamine solution prepared in Example 5 was stored at room temperature (24° to 26° C.) for 3 days. The resultant radioactive diagnostic agent was subjected to thin layer chromatography as in Example 9 and also subjected to examination of the behavior in rats as in Example 10. In both cases, the results were substantially the same as those obtained with a radioactive diagnostic agent prepared in the same manner as above but without storage at room temperature.

EXAMPLE 14

Toxicity of non-radioactive carriers

Each of the non-radioactive carriers prepared in Examples 1 to 3, in case of the non-radioactive carrier prepared in Example 2, after dissolving the same in PBS was intravenously administered to groups of male and female rats of SD strain and groups of male and female mice of ICR strain, each group consisting of 10 animals, respectively in amounts of 1 ml per 100 g of the body weight (corresponding to 400 times the designed dose to human adult) and of 0.5 ml per 10 g of the body weight (corresponding to 2000 times the designed dose to human adult). As control, the same number of groups of animals as above received intravenously the same volume of physiologically saline solution as above. These animals were fed for 10 days, and the variation of the body weight was recorded during this period. No significant difference was produced in the body weight between the medicated group animals and the control group animals. After the said 10 days' observation, all the animals were sacrificed, and abnormality in the internal tissues and organs was examined. No abnormality was found. Thus, the non-radioactive carrier of the invention produces no abnormality even when administered in an amount of 400 to 2000 times of the normal dose.

EXAMPLE 15

Toxicity of $^{67}$Ga-labeled radioactive diagnostic agent

The $^{67}$Ga-labeled radioactive diagnostic agent (i.e. $^{67}$Ga-labeled, human serum albumin-combined deferoxamine) prepared in Example 5 was, after proper attenuation of the radioactivity, subjected to testing of toxicity in the same manner as in Example 14. No significant difference was produced in the body weight between the medicated group animals and the control group animals. After 10 days' observation, all the animals were sacrificed, and abnormality in the internal tissues and organs was examined. No abnormality was found. Thus, the radioactive diagnostic agent of the invention produces no abnormality even when administered in an amount of 300 to 1500 times of the normal dose.

What is claimed is:

1. A radioactive metallic element-labeled, physiologically active substance-combined compound, which consists of deferoxamine, an organic physiologically active substance chemically bonded thereto with or without intervention of any other chemical bonding and a radioactive metallic element bonded to said deferoxamine through a chelating bond.

2. The compound according to claim 1, wherein the physiologically active substance has a carboxyl group and is bonded to deferoxamine by forming a —CONH— linkage between the carboxyl group in the physiologically active substance and the amino group in deferoxamine.

3. The compound according to claim 1, wherein the physiologically active substance has an amino group and is bonded to deferoxamine with intervention of a compound having at least two carbonyl groups by forming a >C=N— linkage between the amino group in the physiologically active substance and an carboxyl group in said compound and also between the amino group in deferoxamine and another carbonyl group in said compound, the >C=N— linkage being thereafter converted into a >CHNH— linkage by reduction.

4. The compound according to claim 1, wherein the physiologically active substance is human serum albumin.

5. The compound according to claim 1, wherein the physiologically active substance is urokinase.

6. The compound according to claim 1, wherein the physiologically active substance is fibrinogen.

7. The compound according to claim 1, wherein the radioactive metallic element is $^{67}$Ga.

8. The compound according to claim 1, wherein the radioactive metallic element is $^{111}$In.

9. A physiologically active substance-combined compound, which consists of deferoxamine and an organic physiologically active substance chemically bonded thereto with or without intervention of any other chemical bonding.

10. The compound according to claim 9, wherein the physiologically active substance has a carboxyl group and is bonded to deferoxamine by forming a —CONH— linkage between the carboxyl group in the physiologically active substance and the amino group in deferoxamine.

11. The compound according to claim 9, wherein the physiologically active substance has an amino group and is bonded to deferoxamine with intervention of a compound having at least two carbonyl groups by forming a >C=N— linkage between the amino group in the physiologically active substance and an carboxyl group in said compound and also between the amino group in deferoxamine and another carbonyl group in said compound, the >C=N— linkage being thereafter converted into a >CHNH— linkage by reduction.

12. A physiologically active substance-combined compound comprising deferoxamine and a physiologically active substance selected from the group consisting of proteins, antibiotics, hormones, saccharides and fatty acids chemically bonded thereto with or without intervention of any other chemical bonding.

13. The compound according to claim 12, and further comprising a radioactive metallic element bonded to said deferoxamine through a chelating bond.

14. The compound according to claim 12, wherein said physiologically active substance is a protein.

15. The compound according to claim 12, wherein said physiologically active substance is an antibiotic.

16. The compound according to claim 12, wherein said physiologically active substance is a hormone.

17. The compound according to claim 12, wherein said physiologically active substance is a saccharide.

18. The compound according to claim 12, wherein said physiologically active substance is a fatty acid.

19. The compound according to claim 12, wherein said physiologically active substance has an active carboxyl group which is bonded with said deferoxamine.

20. The compound according to claim 12, wherein said physiologically active substance has an active amino group which is bonded with said deferoxamine.

21. A method for diagnosing physiological abnormalities which comprises administering to a patient an effective imaging amount of the compound according to claim 1 and imaging said abnormality.

22. A method for diagnosing physiological abnormalities which comprises administering to a patient an effective imaging amount of the compound according to claim 13 and imaging said abnormality.

* * * * *